United States Patent [19]
Ross et al.

[11] Patent Number: 5,877,863
[45] Date of Patent: Mar. 2, 1999

[54] READHEAD FOR A PHOTOMETRIC DIAGNOSTIC INSTRUMENT

[75] Inventors: Gary D. Ross; Nick T. Stock, both of Gwent, United Kingdom

[73] Assignee: Bayer Corporation, Elkhart, Ind.

[21] Appl. No.: 822,189

[22] Filed: Mar. 20, 1997

[51] Int. Cl.$^6$ .................................................. G01N 21/55
[52] U.S. Cl. ......................................................... 356/445
[58] Field of Search ........................... 356/402–411, 420, 356/446–448, 416; 250/226, 227.11–227.32; 385/12, 13

[56] References Cited

U.S. PATENT DOCUMENTS

| | | |
|---|---|---|
| 3,907,503 | 9/1975 | Betts et al. . |
| 4,755,058 | 7/1988 | Shaffer . |
| 5,028,139 | 7/1991 | Kramer et al. . |
| 5,054,487 | 10/1991 | Clarke ...................................... 356/420 |
| 5,165,078 | 11/1992 | Hough et al. . |
| 5,272,518 | 12/1993 | Vincent .................................. 250/226 |
| 5,303,037 | 4/1994 | Taranowski ............................. 356/402 |
| 5,518,689 | 5/1996 | Dosmann et al. . |
| 5,701,181 | 12/1997 | Boiarski et al. . |

OTHER PUBLICATIONS

W. E. Howard, III, "An Introduction To Reflectance Spectroscopy For Dry Phase Reagent Chemistry", *Miles Science Journal*, pp. 33–37.

*Primary Examiner*—K P Hantis
*Attorney, Agent, or Firm*—Roger N. Coe

[57] ABSTRACT

A readhead for a photometric diagnostic instrument for illuminating a target area substantially uniformly via only a single light-emitting diode (20) and receiving light from the target area so that reagent tests may be performed is provided with a housing (12, 14, 16) adapted to be incorporated in a photometric diagnostic instrument, first and second light sources (20) mounted in a fixed position relative to the housing (12, 14, 16), a light guide (26) mounted to receive light from each of the light sources (20) which conveys, when only one of the light sources (20) is illuminated, substantially all of the light from the light source (20) to illuminate a target area substantially uniformly, and a light detector (70) coupled to receive light from the target area. Each of the first and second light sources (20) is composed of only a single light-emitting diode (20) for emitting substantially monochromatic light of a different wavelength.

17 Claims, 2 Drawing Sheets

READHEAD FOR A PHOTOMETRIC DIAGNOSTIC INSTRUMENT

BACKGROUND OF THE INVENTION

The present invention relates to a readhead for a photometric diagnostic instrument, such as a reflectance spectroscope, for performing tests on a sample of body fluid to be analyzed.

It is useful for various medical diagnostic purposes to utilize a reflectance spectroscope to analyze samples of body fluid, for example, to detect on immunotest strips or chemistry test strips the presence of blood in a person's urine. Conventional reflectance spectroscopes have been used to detect the presence of blood in a urine sample disposed on a reagent pad. Any blood present in the urine reacts with the reagent on the reagent pad, causing the reagent pad to change color to an extent which depends on the concentration of the blood. For example, in the presence of a relatively large concentration of blood, such a reagent pad may change in color from yellow to dark green.

One conventional reflectance spectroscope detects the concentration of the blood by illuminating the reagent pad and detecting, via a conventional reflectance detector, the amount of light received from the reagent pad, which is related to the color of the reagent pad. Based upon the magnitude of the reflectance signal generated by the reflectance detector, the spectroscope assigns the urine sample to one of a number of categories, e.g. a first category corresponding to no blood, a second category corresponding to a small blood concentration, a third category corresponding to a medium blood concentration, and a fourth category corresponding to a large blood concentration.

A prior art reflectance spectroscope has been provided with an optical system in the form of a read head in which a light bulb is disposed directly above the reagent pad to be tested and a reflectance detector is disposed at a 45° angle to the horizontal surface of the reagent pad. Light from that spectroscope passes through a first vertical optical path from the illumination source to the reagent pad and through a second optical path, disposed 45° with respect to the first optical path, from the reagent pad to the reflectance detector.

Other devices have been designed to illuminate a reagent pad. For example, U.S. Pat. No. 4,755,058 to Shaffer discloses a device for illuminating a surface and detecting the intensity of light emitted from the surface. The surface is directly illuminated by a plurality of light-emitting diodes disposed at an acute angle relative to the surface. U.S. Pat. No. 5,518,689 to Dosmann, et al. discloses a diffused light reflectance readhead in which one or more light-emitting diodes are used to illuminate a reagent pad and in which light from the reagent pad is detected by a light sensor.

SUMMARY OF THE INVENTION

The invention is directed to a readhead for a photometric diagnostic instrument for illuminating a target area substantially uniformly via only a single light-emitting diode and receiving light from the target area so that reagent tests may be performed. Since the readhead has the capability to uniformly illuminate the entire target area, which may correspond to a reagent strip having a number of reagent pads disposed thereon, it is not necessary to provide means for moving the reagent strip relative to the light-emitting diode.

In one aspect of the invention, the readhead is provided with a housing adapted to be incorporated in a photometric diagnostic instrument, first and second light sources mounted in a fixed position relative to the housing, a light guide mounted to receive light from each of the light sources which conveys, when only one of the light sources is illuminated, substantially all of the light from the light source to illuminate the target area substantially uniformly, and a light detector coupled to receive light from the target area. Each of the first and second light sources is composed of only a single light-emitting diode for emitting a substantially monochromatic light of a particular wavelength.

The light guide may include means for randomizing the light emitted by the light sources, such as a diverging light guide having a relatively small width at a point adjacent an inlet of the light guide and a relatively large width at a point adjacent an outlet of the light guide. The light guide may be composed of a clear material having a shape which causes the light emitted by the light sources to be totally internally reflected from the inlet of the light guide to the outlet of the light guide.

The readhead may also include means for directing light from the target area to the light detector in the form of a mirror positioned to receive light from the target area and a lens positioned to receive light reflected by the mirror and to transmit light to the light detector.

In another aspect of the invention, the readhead has a housing adapted to be incorporated in a photometric diagnostic instrument, a light source comprising a light-emitting diode mounted in a fixed position relative to the housing, a light guide for conveying light emitted from the light-emitting diode to a target area, and a light detector coupled to receive light from the target area. The light guide is mounted in a fixed position relative to the light source and includes means for randomizing the light emitted by the light-emitting diode.

In a further aspect of the invention, the readhead is provided with a housing adapted to be incorporated in a photometric diagnostic instrument, a light source comprising a lensless light-emitting diode mounted in a fixed position relative to the housing, a light guide mounted in a fixed position relative to the light source for conveying light from the light source to a target area, and a light detector coupled to receive light from the target area.

These and other features and advantages of the present invention will be apparent to those of ordinary skill in the art in view of the detailed description of the preferred embodiment, which is made with reference to the drawings, a brief description of which is provided below.

DETAILED DESCRIPTION OF A PREFERRED EMBODIMENT

Figure 1:
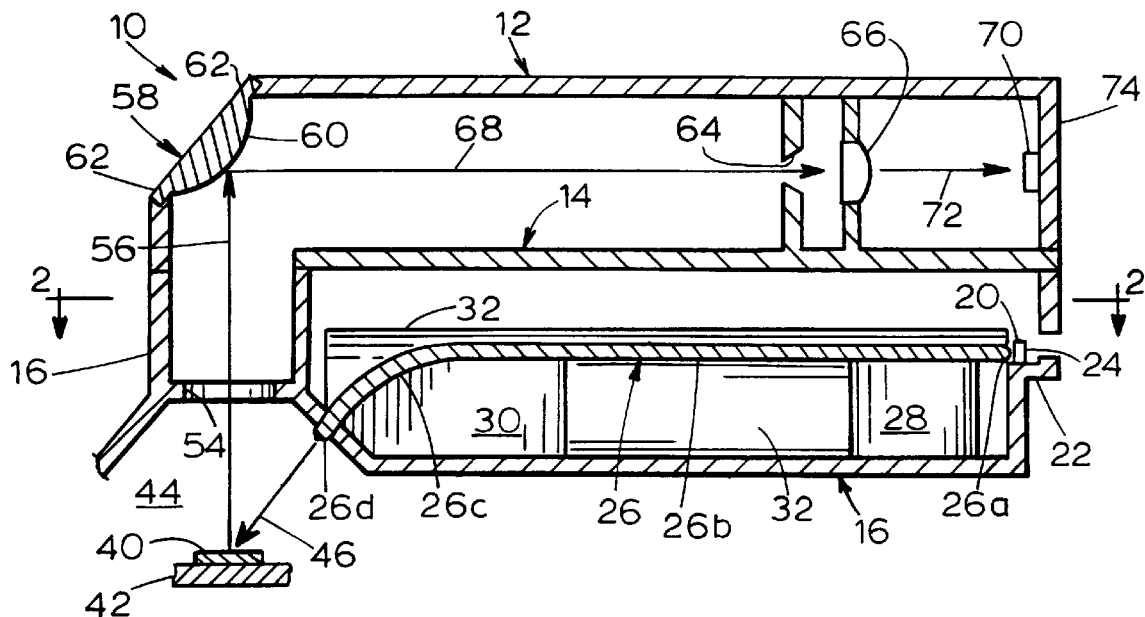
FIG. 1 is a cross-sectional side view of a preferred embodiment of a readhead in accordance with the invention.
Figure 2:
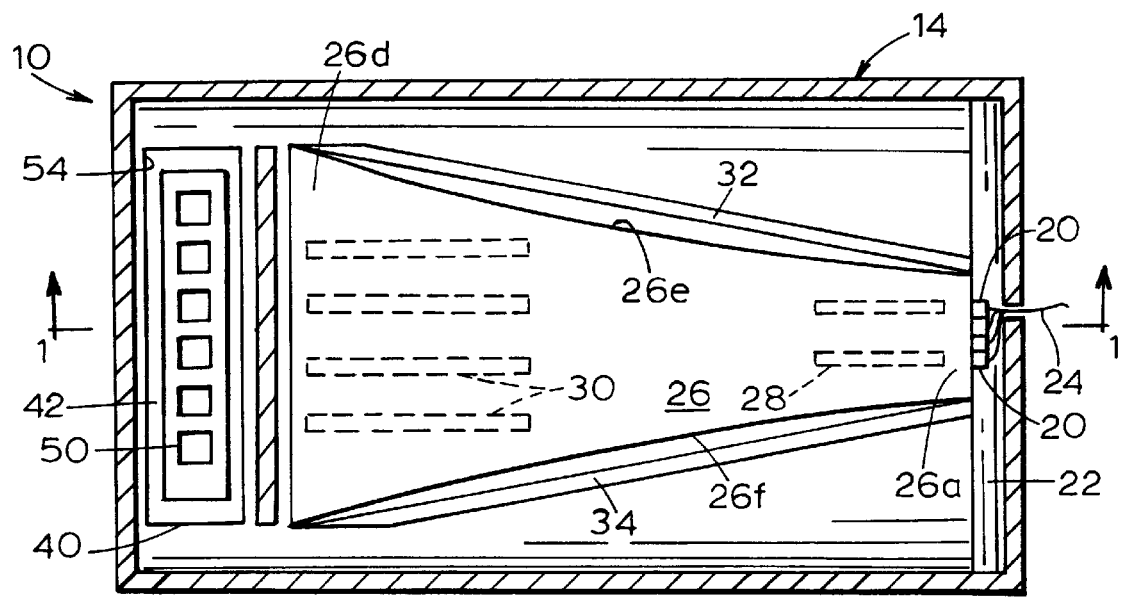
FIG. 2 is a cross-sectional top view of a portion of the readhead taken along lines 2—2 in FIG. 1.

FIGS. 1 and 2 illustrate a preferred embodiment of a readhead 10 for a photometric diagnostic instrument such as a reflectance spectroscope. The readhead 10 has a housing formed from an upper housing portion 12, a middle housing portion 14, and a lower housing portion 16 which may be connected together in any conventional manner. The housing portions 12, 14, 16 may be injection-molded parts comprising black plastic to substantially absorb any errant light rays that are incident upon the housing. While the housing portions 12, 14, 16 are shaped and adapted to be incorporated into a photometric diagnostic instrument, the detailed shape of the housing portions 12, 14, 16 is not considered important to the invention, and additional structures, such as holes and tabs, could be included with the housing portions 12, 14, 16 to facilitate the integration of the housing portions 12, 14, 16 into the diagnostic instrument.

Four light sources in the form of light-emitting diodes (LEDs) 20 are supported on a ledge 22 formed in the lower housing portion 16. The LEDs 20 could be supported on a printed circuit board (not shown). Each of the LEDs 20 is designed to emit monochromatic radiation of a different wavelength, corresponding to red light, green light, blue light and infrared. The wavelength of the light emitted may vary from about 400 nanometers (for blue light) to about 1,000 nanometers (for infrared). Each of the LEDs 20 may be selectively turned on and off via a plurality of wires 24 connected between the LEDs 20 and an activation circuit (not shown).

The LEDs 20 are disposed directly adjacent and in very close proximity with an inlet end 26a of a light guide 26 into which light from the LEDs 20 is radiated. As shown in FIG. 1, the light guide 26 has a relatively long, substantially planar portion 26b and a portion 26c that curves downwardly towards an outlet end 26d of the light guide 26. As shown in FIG. 2, which is a top cross-sectional view of a portion of the readhead 10, the light guide 26 has a pair of curved sides 26e, 26f that diverge outwardly from the inlet end 26a to the outlet end 26d of the light guide 26.

The light guide 26, which may be an injection-molded part composed of clear plastic such as acrylic or polycarbonate, conducts substantially all light that enters its inlet end 26a to its outlet end 26d via total internal reflection. To prevent any internally reflected light from exiting the light guide 26 between its inlet 26a and outlet 26d, the exterior of the light guide 26 could optionally be coated with a highly reflective coating, such as silver.

The light guide 26 is supported within the lower housing portion 15 by a pair of supports 28 disposed beneath the light guide 26 at a point near its inlet end 26a and a plurality of supports 30 disposed beneath the light guide 26 at a point near its outlet end 26d. The supports 28, 30 may be integrally formed with the lower housing portion 16. As shown in FIG. 2, the light guide 26 is positioned between a pair of angled guide walls 32, 34.

As shown in FIG. 1, light is emitted from the outlet end 26d of the light guide 26 towards a reagent strip 40 disposed on a support 42 in an illumination chamber 44, as indicated by an arrow 46. The support 42 is nonmovable relative to the housing portions 12, 14, 16. The reagent strip 40 has a thin, non-reactive substrate on which a number of reagent pads 50 are fixed. Each reagent pad 50 is composed of a relatively absorbent material impregnated with a respective reagent, each reagent and reagent pad 50 being associated with a particular test to be performed. When urinalysis tests are performed, they may include, for example, a test for leukocytes in the urine, a test of the pH of the urine, a test for blood in the urine, etc. When each reagent pad 50 comes into contact with a urine sample, the pad changes color over a time period, depending on the reagent used and the characteristics of the urine sample. The reagent strip 40, which is conventional, may be a Multistix® reagent strip commercially available from Bayer Corporation.

Light from the reagent strip 40 passes through a rectangular opening 54 formed in the lower housing portion 16, in a direction indicated by an arrow 56, towards a mirror element 58 fixed in the upper left corner of the upper housing portion 12. The mirror element 58 is composed of a cylindrical mirror 60 and a pair of mounting tabs 62 connected to the mirror 60. The mirror element 58, which may be a plastic injection molded part having the curved portion 60 being coated with a highly reflective material, extends approximately the length of the aperture 54 shown in FIG. 2. The mirror 60 reflects light that is incident upon it from the reagent strip 40 through a square aperture 64 formed in the middle housing portion 14 and to a lens 66 supported by the middle housing portion 14, as indicated by an arrow 68. One side of the lens 66 has a planar surface and the other side of the lens 66 has a convexly curved (aspheric) surface. Light passing through the lens 66 is transmitted to a light detector array 70, as indicated by an arrow 72.

The detector array 70, which is fixed to a side wall 74 of the upper housing portion 12, may comprise a conventional detector array, such as a TSL 1402 commercially available from Texas Instruments, which is composed of 256 individual light detectors aligned in a single horizontal row.

In operation, only one of the LEDs 20 is illuminated at a time, and the illumination provided by that single LED 20 is sufficient to uniformly illuminate the reagent strip 40 to an extent that allows the detector array 70 to detect enough light from the reagent strip 40 to have the reagent tests described above satisfactorily performed. Each individual light detector in the array 70 senses light from a particular point along the length of the reagent strip 40. For example, to detect light from the lowermost reagent pad 50 shown in FIG. 2, a number of the light detectors on the corresponding end of the detector array 70 would be activated. Light from all of the reagent pads 50 could be simultaneously detected by activating all of the detectors in the array 70.

The cross-sectional shape of the mirror 60 is curved so that each light detector in the detector array 70 detects light from a wider portion of the reagent strip 40 than if a mirror having a straight cross-sectional shape were used. However, depending on the particular design of the readhead 10, a straight mirror could be used instead of the cylindrically curved mirror 60.

Referring to FIG. 2, the light guide 26 is diverging, having a relatively small width at its inlet end 26a and a relatively large width at its outlet end 26d. The fact that the light guide 26 is diverging acts to 1) spread the light from a single one of the LEDs 20 along a relatively large length, corresponding to the length of the outlet end 26d, and 2) cause the light rays emitted by one of the LEDs 20 to be randomized, thus providing more uniform illumination at the target area in which the reagent strip 40 is located, by causing some of the light rays to be internally reflected within the light guide 26 at different angles.

With respect to feature 2), it should be understood that in a light guide having diverging side walls, a single light ray may be reflected from the walls at different angles (i.e. at successively shallower angles of incidence with respect to the side walls as the light ray passes from the inlet to the outlet), thus increasing the randomness of the light rays and the uniformity of the illumination.

Figure 5:
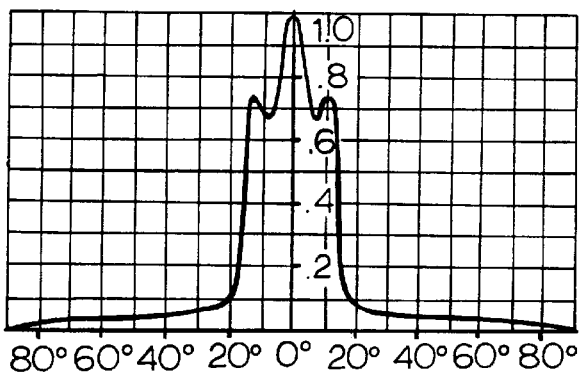
FIG. 5 is a graph of the light intensity versus emission angle for a conventional light-emitting diode having a lens.
Figure 6:
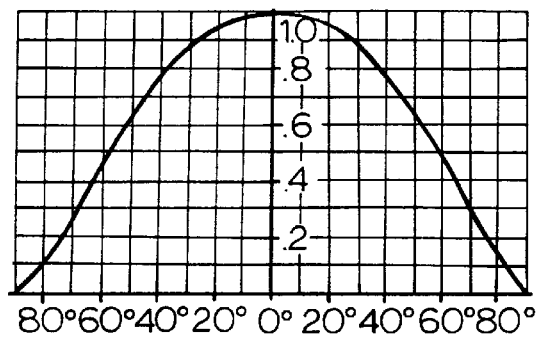
FIG. 6 is a graph of the light intensity versus emission angle for a lensless light-emitting diode.

The LEDs 20 preferably comprise lensless LEDs, such as surface-mount LEDs. Conventional LEDs are typically provided with a lens which covers the light-emitting component of the LED. Such lenses provide a relatively high degree of directionality, as shown in FIG. 5, which is a graph of the relative intensity of light emitted by a lensed LED versus the emission angle of the light. At emission angles of greater than about 20°, the light has a very weak intensity. A lensless LED acts more of a Lambertian source by exhibiting a much lower degree of directionality, as shown in FIG. 6, which is a graph of the relative intensity of light emitted by a lensless LED versus the emission angle.

Figure 7:
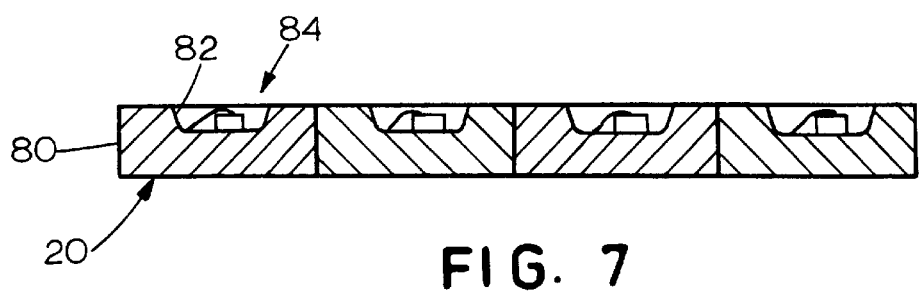
FIG. 7 is a cross-sectional side view of a lensless light-emitting diode array of the readhead.

FIG. 7 illustrates the structure of the conventional lensless LEDs 20. Referring to FIG. 7, each LED 20 is shown to generally comprise a substrate 80 having a cavity 82 formed therein, with the light-emitting structure 84 being disposed within the cavity 82 and with no lens covering the cavity 82 or the light-emitting structure 84.

In one particular embodiment of the readhead 10, the cross-sectional shape of the mirror 60 is circular, having a radius of curvature of about 11 millimeters (mm), and the mirror 60 is disposed 22.5 mm above the reagent strip 40 and approximately 79 mm to the left of the aperture 64 (FIG. 1). The aperture 64 is square, having a length of four mm on each side, and is disposed to the left of the lens 66 by about four mm. The width of the lens 66 at its thickest point is 4.26 mm, and the lens 66 is spaced from the detector array 70 by about 20 mm and has a magnification factor of about 5.5.

Figure 3:
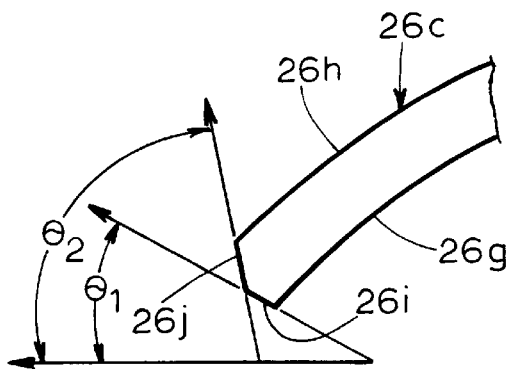
FIG. 3 illustrates the structure of the outlet end of a light guide of the readhead.
Figure 4:
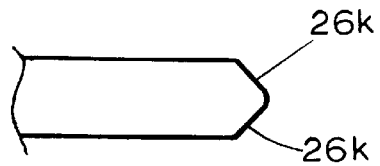
FIG. 4 illustrates the structure of the inlet end of the light guide of the readhead.

In the above particular embodiment, the width of the light guide 26 at its inlet end 26a is 25 millimeters (mm); the width of the light guide 26 at its outlet end 26d is 83 mm (in this case the length of the reagent strip is 90 mm); and the length of the light guide 26 (in the horizontal direction) is 105 mm. The side wall 26f (which is symmetrical to the side wall 26e) has a circular curvature having a radius of 574 mm taken from a center point located (when the light guide 26 is viewed from above as shown in FIG. 2) 537.6 mm below and 201.6 mm to the right of the lower left edge of the light guide 26. The lower side 26g (FIG. 3) of the curved portion 26c of the light guide 26 has a circular curvature having a radius of 22.9 mm taken from a center point located 84.1 mm to the left of the inlet end 26a of the light guide 26 and 26.4 mm below the top surface of the light guide 26. The upper side 26h of the curved portion 26c has a circular curvature below a radius of 40 mm taken from a center point located 78.7 mm to the left of the inlet end 26a of the light guide 26 and 40 mm below the top surface of the light guide 26. Referring to FIG. 3, the outlet end 26d has a first surface 26i that is disposed at an angle $\theta_1$ of 31.5° and a second surface 2bj that is disposed at an angle $\theta_2$ of 77.6° with respect to the horizontal. Referring to FIG. 4, the inlet end 26a has a pair of symmetrically disposed angled surfaces 26k.

Although one specific structure for the components of the readhead 10 has been described in detail above, other suitable structures could be used. Such structures could be designed utilizing conventional ray-trace computer programs (which automatically illustrate the direction in which numerous light rays are reflected) to achieve a suitable design which provides the desired uniformity of the light emitted by the light guide.

In an alternative design, the mirror element 58 could be omitted, and the detectors 70 could be placed directly above the aperture 54.

Additional modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A readhead for a photometric diagnostic instrument for illuminating a target area and receiving light from the target area, said readhead comprising:

a housing (12, 14, 16) adapted to be incorporated in said photometric diagnostic instrument;

a first light source (20) mounted in a fixed position relative to said housing (12, 14, 16), said first light source (20) being composed of only a single light-emitting diode (20) for emitting substantially monochromatic light of a first wavelength;

a second light source (20) mounted in a fixed position relative to said housing (12, 14, 16), said second light source (20) being composed of only a single light-emitting diode (20) for emitting substantially monochromatic light of a second wavelength substantially different from said first wavelength;

light guide means (26), mounted to receive light from each of said light sources (20), for conveying, when only one of said light sources (20) is illuminated, substantially all of said light from said one light source (20) to a target area so that said target area is illuminated substantially uniformly, said light guide means (26) comprising a diverging light guide (26) having a relatively small width at a point adjacent an inlet of said diverging light guide (26) and a relatively large width at a point adjacent an outlet of said diverging light guide (26); and a light detector (70) coupled to receive light from said target area.

2. A readhead as defined in claim 1 wherein said light guide means (26) comprises means for substantially uniformly illuminating a rectangular target area having a length and a width, said length being at least about twice as large as said width.

3. A readhead as defined in claim 1 additionally comprising support means (42) for supporting a reagent strip in said target area, said support means (42) being nonmovable relative to said housing (12, 14, 16).

4. A readhead as defined in claim 1 wherein said light guide means (26) comprises a clear material having a shape which causes said light emitted by said one light source (20) to be totally internally reflected from an inlet of said light guide means (26) to an outlet of said light guide means (26).

5. A readhead as defined in claim 1 additionally comprising means for directing light from said target area to said light detector (70), said light-directing means comprising:

a mirror (58) positioned to receive light from said target area; and a lens (66) positioned to receive light reflected by said mirror (58) and to transmit light to said light detector (70).

6. A readhead as defined in claim 1 additionally comprising means for directing light from said target area to said light detector (70), said light-directing means comprising a mirror (58) positioned to receive light from said target area, said mirror (58) having a cylindrically curved surface.

7. A readhead for a photometric diagnostic instrument for illuminating a target area and receiving light from said target area, said readhead comprising:

a housing (12, 14, 16) adapted to be incorporated in said photometric diagnostic instrument;

a light source (20) mounted in a fixed position relative to said housing, said light source (20) comprising a light-emitting diode (20) for emitting light;

a diverging light guide (26), mounted to receive light from said light source (20), adapted to convey substantially all of said light from said light source (20) to a target area so that said target area is illuminated substantially uniformly, said diverging light guide (26) having a relatively small width at a point adjacent an inlet of said diverging light guide (26) and a relatively large width at a point adjacent an outlet of said diverging light guide (26); and a light detector (70) coupled to receive light from said target area.

8. A readhead as defined in claim 7 wherein said light guide (26) comprises a clear material having a shape which causes said light emitted by said light source (20) to be totally internally reflected from said inlet of said light guide (26) to said outlet of said light guide (26).

9. A readhead as defined in claim 7 additionally comprising:

a mirror (58) positioned to receive light from said target area; and a lens (66) positioned to receive light reflected by said mirror (58) and to transmit light to said light detector (70).

10. A readhead for a photometric diagnostic instrument for illuminating a target area and receiving light from said target area, said readhead comprising:

a housing (12, 14, 16) adapted to be incorporated in said photometric diagnostic instrument;

a light source (20) mounted in a fixed position relative to said housing (12, 14, 16), said light source (20) comprising a lensless light-emitting diode (20);

a light guide (26), mounted in a fixed position relative to said light source (20), for conveying light from said light source (20) to a target area; and a light detector (70) coupled to receive light from said target area.

11. A readhead as defined in claim 10 wherein said light guide (26) includes means for randomizing said light emitted by said light-emitting diode (20).

12. A readhead as defined in claim 10 wherein said light guide (26) comprises a diverging light guide (26) having a relatively small width at a point adjacent an inlet of said diverging light guide (26) and a relatively large width at a point adjacent an outlet of said diverging light guide (26).

13. A readhead as defined in claim 10 wherein said light guide (26) has a pair of non-parallel sidewalls.

14. A readhead as defined in claim 10 wherein said light guide (26) comprises a clear material having a shape which causes said light emitted by said light source (20) to be totally internally reflected from an inlet of said light guide (26) to an outlet of said light guide (26).

15. A readhead as defined in claim 10 additionally comprising:

a mirror (58) positioned to receive light from said target area; and a lens (66) positioned to receive light reflected by said mirror (58) and to transmit light to said light detector (70).

16. A readhead as defined in claim 10 additionally comprising a mirror (58) positioned to receive light from said target area, said mirror (58) having a cylindrically curved surface.

17. A readhead as defined in claim 10 wherein said target area comprises a rectangular area having a length and a width, said length of said rectangular area being at least about four times as large as said width of said rectangular area, and wherein said light guide (26) conveys substantially all of said light emitted from said light-emitting diode (20) to said rectangular area.

* * * * *